(12) United States Patent  (10) Patent No.: US 8,475,376 B2
Mikami  (45) Date of Patent: Jul. 2, 2013

(54) MEDICAL IMAGING APPARATUS

(75) Inventor: Yuji Mikami, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 873 days.

(21) Appl. No.: 12/458,812

(22) Filed: Jul. 23, 2009

(65) Prior Publication Data

US 2010/0030078 A1  Feb. 4, 2010

(30) Foreign Application Priority Data

Jul. 31, 2008  (JP) ................................. 2008-198174

(51) Int. Cl.
*A61B 8/00* (2006.01)
(52) U.S. Cl.
USPC ........... 600/437; 600/425; 600/427; 600/443; 600/444; 600/407
(58) Field of Classification Search
USPC .................................. 600/425, 437, 443–444
See application file for complete search history.

(56) References Cited

U.S. PATENT DOCUMENTS

| 6,574,499 B1 | 6/2003 | Dines et al. | |
|---|---|---|---|
| 2004/0034307 A1* | 2/2004 | Johnson et al. | 600/459 |
| 2004/0181152 A1* | 9/2004 | Zhang et al. | 600/437 |
| 2005/0113684 A1 | 5/2005 | Lokhandwalla et al. | |

FOREIGN PATENT DOCUMENTS

| JP | 2003-260046 A | 9/2003 |
|---|---|---|
| JP | 2003-310614 A | 11/2003 |

\* cited by examiner

*Primary Examiner* — Unsu Jung
*Assistant Examiner* — Christopher Cook
(74) *Attorney, Agent, or Firm* — Jean C. Edwards, Esq.; Edwards Neils PLLC

(57) ABSTRACT

In a medical imaging apparatus for imaging mammary gland and breast while compressing the breast with a compression plate, the posture of an ultrasonic probe relative to the compression plate is kept constant and the moving motion of the ultrasonic probe is stabilized. The apparatus includes: an imaging stage; a compression plate; an ultrasonic probe provided to maintain acoustic connection to the compression plate, for transmitting ultrasonic waves according to drive signals and receiving ultrasonic echoes to output reception signals; an ultrasonic imaging unit for supplying the drive signals to the ultrasonic probe and generating image data based on the reception signals; a detecting unit for detecting a location and/or a posture of the ultrasonic probe relative to the compression plate; and a control unit for controlling the location and/or the posture of the ultrasonic probe based on a detection result of the detecting unit.

5 Claims, 6 Drawing Sheets

MEDICAL IMAGING APPARATUS

CROSS-REFERENCE TO RELATED APPLICATION

The present application claims priority from Japanese Patent Application No. 2008-198174 filed on Jul. 31, 2008, the contents of which are incorporated herein by reference in their entirety.

BACKGROUND OF THE INVENTION

1. Field of the Invention

The present invention relates to a medical imaging apparatus for imaging mammary gland and breast while compressing the breast with a compression plate, for diagnoses of breast cancer or the like.

2. Description of a Related Art

Conventionally, an imaging method using radiation (X-ray, α-ray, β-ray, γ-ray, electron ray, ultraviolet ray, or the like) is utilized in various fields, and particularly, in the medical field, the imaging method is one of the most important means for diagnoses. Radiation images obtained by X-ray imaging (X-ray mammography) of breasts for breast cancer diagnoses are useful for finding calcification as a precursor of mass and cancer, but finding calcification may be difficult depending on mammary gland density or the like of an object to be inspected. Accordingly, using radiation and ultrasonic wave in combination to make diagnoses based on both radiation images and ultrasonic images has been studied. X-ray mammography and ultrasonic imaging have the following features, respectively.

X-ray mammography is suitable for exposing calcification as one of early symptoms of a cancer, and enables detection with high sensitivity and high resolving power. Especially, in the case where mammary gland tissues have become atrophied and replaced with fat (so-called "fat breast") as is the case of postmenopausal women, more information can be obtained by X-ray mammography. However, the X-ray imaging has a disadvantage that detection capability of specific natures of tissues (tissue properties) is low.

Further, in an X-ray image, mammary glands are expressed in homogeneous soft tissue density, and thus, the detection of tumor mass is difficult in the case where mammary glands have developed (so-called, "dense breast") as is the case of adolescent to premenopausal women. Furthermore, in X-ray mammography, only two-dimensional images in which an object to be inspected as a solid is projected on a plane can be obtained. On this account, even when a tumor mass is found, it is difficult to grasp information on the location, size, and so on of the tumor mass in the depth direction.

On the other hand, in ultrasonic imaging, specific natures of tissues (e.g., the difference between a cystic tumor and a solid matter) can be detected, and also a lobular cancer can be detected. Further, real time observation of images and three-dimensional image generation are possible. However, ultrasonic imaging examination often depends on the skill of an operator such as a doctor in accuracy and provides low reproducibility. Further, it is difficult to observe minute calcification in an ultrasonic image.

As described above, X-ray mammography examination and ultrasonic imaging examination have both merits and demerits, and therefore, it is desirable that both examinations are performed for reliably finding breast cancer.

Since the X-ray mammography examination is performed while the object (breast) is compressed by a compression plate, in order to make diagnoses based on X-ray images and ultrasonic images of the object in the same condition, the ultrasonic imaging examination is necessary to be performed in the same condition as that when the X-ray mammography examination is performed, that is, while the object (breast) is compressed by the compression plate. Accordingly, a medical imaging apparatus for imaging mammary gland and breast by using radiation and ultrasonic waves in combination is considered.

In the medical imaging apparatus, ultrasonic waves transmitted from an ultrasonic probe provided close to the compression plate pass through the compression plate and reach a breast, and ultrasonic echoes reflected by the breast pass through the compression plate again and are received by the ultrasonic probe. Here, when an air layer exists between the ultrasonic probe and the compression plate, ultrasonic waves are reflected at a boundary of the air layer and image quality is deteriorated in the ultrasonic images. Accordingly, echo gel or the like is applied to the compression plate.

As a related technology, U.S. Pat. No. 6,574,499 B1 discloses a mammography apparatus for generating a three-dimensional image by a triaxial-controlled ultrasound probe acquiring ultrasound images while moving along a curved compression paddle. However, in the mammography apparatus, posture control such as controlling the tilt of the ultrasound probe is not performed, and therefore, the partial floating or the like of the ultrasound probe cannot be prevented.

Further, U.S. Patent Application Publication US 2005/0113684 A1 discloses a medical imaging system for acquiring ultrasound images by an ultrasound probe automatically scanning on a compression paddle. According to the medical imaging system, the ultrasound probe is held in an interface assembly including a tilting suspension structure and spherical contacting elements, the ultrasound probe is moved with the contacting elements in contact with the compression paddle, and thereby, the posture of the ultrasound probe is kept constant with respect to the deformed compression paddle such that a constant gap between the ultrasound probe and the compression paddle is maintained.

In U.S. Pat. No. 6,574,499 B1 and US2005/0113684 A1, the ultrasound probe or the contacting elements moves constantly in contact with the compression paddle, and it is conceivable that the motion is unstable because the drive load becomes larger due to friction between them, resistance of echo gel, and so on. Further, scratches and abrasions on the respective parts due to friction are also concerned.

SUMMARY OF THE INVENTION

The present invention has been achieved in view of the above-mentioned problems. A purpose of the present invention is, in a medical imaging apparatus for imaging mammary gland and breast while compressing the breast with a compression plate, to keep the posture of an ultrasonic probe relative to the compression plate constant and stabilize the moving motion of the ultrasonic probe.

In order to accomplish the above-mentioned purpose, a medical imaging apparatus according to one aspect of the present invention includes: an imaging stage on which an object to be inspected is mounted; a compression plate having a first surface that compresses the object and a second surface opposed to the first surface, for compressing the object between the imaging stage and itself; an ultrasonic probe provided to maintain acoustic connection to the second surface of the compression plate, for transmitting ultrasonic waves according to drive signals and receiving ultrasonic echoes generated when the transmitted ultrasonic waves are reflected by the object to output reception signals; ultrasonic imaging means for supplying the drive signals to the ultrasonic probe and generating image data representing an ultrasonic image based on the reception signals outputted from the ultrasonic probe; detecting means for detecting a location and/or a posture of the ultrasonic probe relative to the compression plate; and control means for controlling the location and/or the posture of the ultrasonic probe relative to the compression plate based on a detection result of the detecting means.

According to the one aspect of the present invention, since the detecting means for detecting the location and/or the posture of the ultrasonic probe relative to the compression plate and the control means for controlling the location and/or the posture of the ultrasonic probe relative to the compression plate based on the detection result of the detecting means are provided, the posture of an ultrasonic probe relative to the compression plate can be kept constant and the moving motion of the ultrasonic probe can be stabilized.

DESCRIPTION OF THE PREFERRED EMBODIMENTS

Hereinafter, preferred embodiments of the present invention will be explained in detail with reference to the drawings. The same reference numbers are assigned to the same component elements and the description thereof will be omitted.

Figure 1:
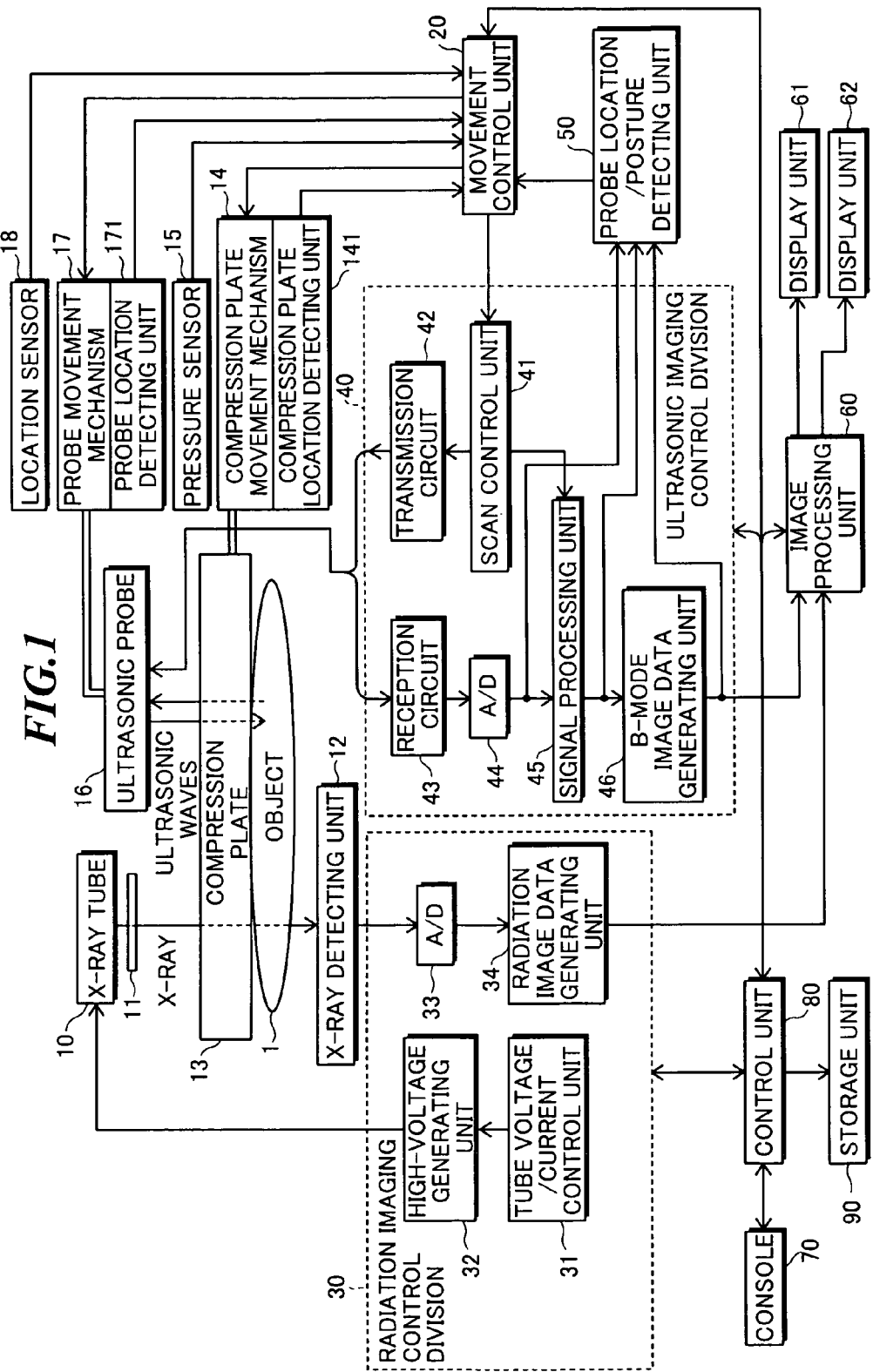
FIG. 1 is a block diagram showing a configuration of a medical imaging apparatus according to one embodiment of the present invention.

FIG. 1 is a block diagram showing a configuration of a medical imaging apparatus according to one embodiment of the present invention. The medical imaging apparatus has both a function of a radiation mammography apparatus for applying radiation to a breast and detecting the radiation transmitted through the breast to generate a radiation image, and a function of an ultrasonic diagnostic apparatus for transmitting ultrasonic waves to the breast and receiving ultrasonic echoes reflected within the breast to generate ultrasonic images. As below, the case of using an X-ray as radiation will be explained, however, α-ray, β-ray, γ-ray, electron ray, ultraviolet ray, or the like may be used.

As shown in FIG. 1, the medical imaging apparatus includes, in an imaging division, an X-ray tube 10, a filter 11, an X-ray detecting unit 12 for detecting an X-ray generated by the X-ray tube 10 and transmitted through an object to be inspected 1, a compression plate 13 for compressing a breast as the object, a compression plate movement mechanism 14 for moving the compression plate 13, a pressure sensor 15 for detecting pressure applied to the compression plate 13, an ultrasonic probe 16 including plural ultrasonic transducers for transmitting and receiving ultrasonic waves, a probe movement mechanism 17 for moving the ultrasonic probe 16, and a location sensor 18 for detecting the location of the ultrasonic probe 16.

Further, the medical imaging apparatus includes a movement control unit 20 for controlling the compression plate movement mechanism 14, the probe movement mechanism 17, and soon, a radiation imaging control division 30, an ultrasonic imaging control division 40, a probe location/posture detecting unit 50, an image processing unit 60, display units 61 and 62, a console 70, a control unit 80, and a storage unit 90.

Figure 2:
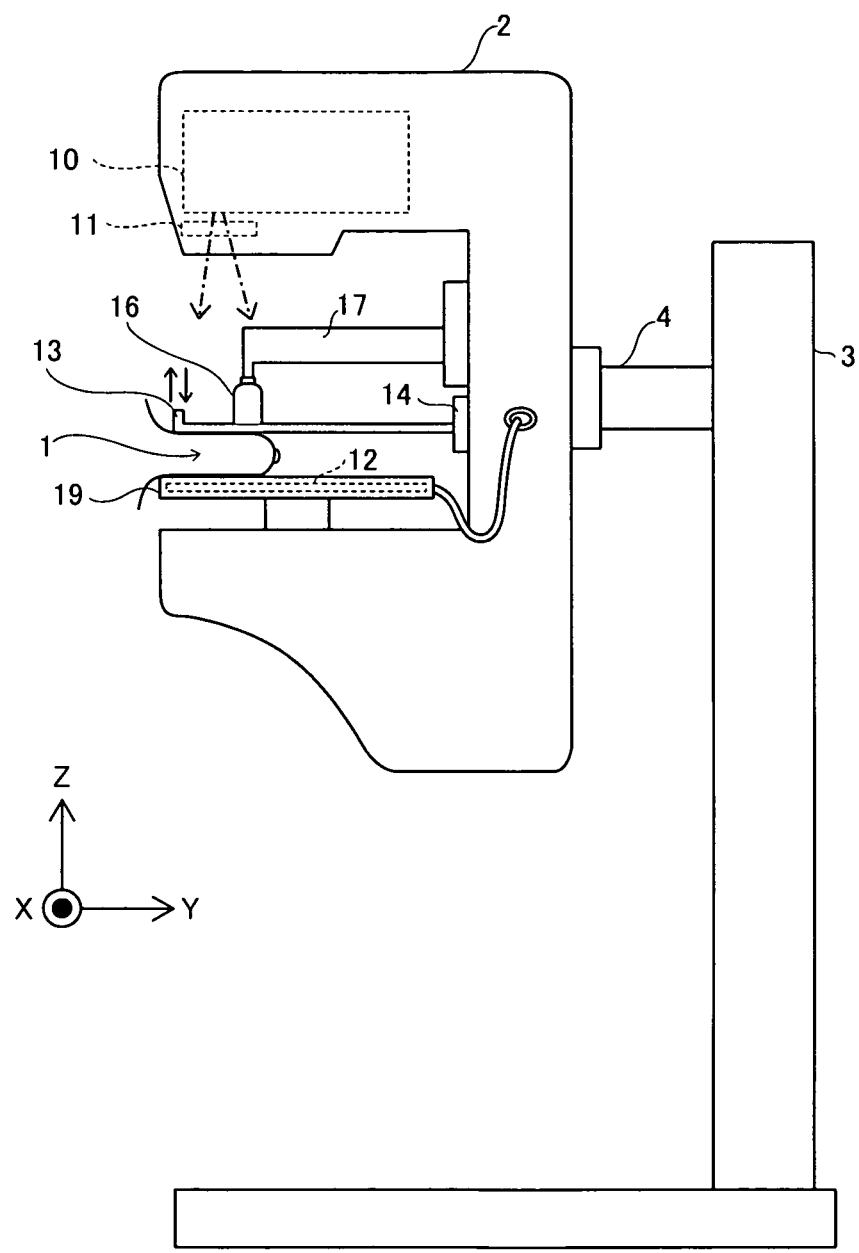
FIG. 2 is a side view showing an appearance of an imaging division of the medical imaging apparatus as shown in FIG. 1.

FIG. 2 is a side view showing an appearance of the imaging division of the medical imaging apparatus as shown in FIG. 1. As shown in FIG. 2, the imaging division of the medical imaging apparatus includes an arm part 2, a supporting base 3 for holding the arm part 2 movably in the vertical direction (Z-axis direction), and a shaft part 4 for connecting the arm part 2 to the supporting base 3. The arm part 2 is provided with the X-ray tube 10, the filter 11, the X-ray detecting unit 12, an imaging stage 19 on which an object 1 to be inspected is mounted, the compression plate 13 for compressing the object 1 between the imaging stage 19 and itself, the compression plate movement mechanism 14 for moving the compression plate 13, the ultrasonic probe 16, and the probe movement mechanism 17 for moving the ultrasonic probe 16 in the X-axis, Y-axis, and Z-axis directions. Here, the X-ray tube 10 and the filter 11 form a radiation emitting unit.

The X-ray tube 10 emits an X-ray when a tube voltage is applied thereto. The filter 11 is made of a material such as molybdenum (Mo), rhodium (Rh), or the like and selectively transmits a desired wavelength component among plural wavelength components contained in the X-ray emitted by the X-ray tube 10. The X-ray detecting unit 12 is a flat panel detector (FPD) for imaging an X-ray image by detecting the X-ray transmitted through the object 1 at plural detection points in a two-dimensional region. The X-ray radiated from the X-ray tube 10 and transmitted through the object 1 is applied to the respective detection points, and thereby, detection signals having magnitudes corresponding to the intensity of the X-ray are outputted from the X-ray detecting unit 12. The detection signals are inputted via a cable to the radiation imaging control division 30 (FIG. 1).

The compression plate 13 has a compression surface (the lower surface in FIG. 2) for compressing the object 1 along the radiation direction of the X-ray and a surface opposed to the compression surface (the upper surface in FIG. 2). The compression plate 13 is provided substantially in parallel to the imaging stage 19, and the compression plate movement mechanism 14 moves the compression plate 13 substantially in the vertical direction (Z-axis direction) under the control of the movement control unit 20 (FIG. 1). The pressure sensor 15 (FIG. 1) detects the pressure applied to the compression plate 13, and the movement control unit 20 controls the compression plate movement mechanism 14 based on the detection result. The object (breast) 1 is sandwiched by the compression plate 13 and the imaging stage 19, and X-ray imaging and ultrasonic imaging are performed with the homogeneous thickness of the breast.

Here, the compression plate 13 is necessary to be optically transparent for positioning when the breast is compressed or confirmation of the compression state, and desirably formed of a material that transmits the X-ray radiated from the X-ray tube 10 and easily propagates ultrasonic waves to be transmitted from the ultrasonic probe 16. As a material of the compression plate 13, a resin such as polycarbonate, acryl, or polymethylpentene, having a suitable value in acoustic impedance that affects the reflectance of ultrasonic waves and a suitable value in attenuation coefficient that affects the attenuation of ultrasonic waves may be used, for example.

The ultrasonic probe 16 includes one-dimensionally or two-dimensionally arranged plural ultrasonic transducers. Each ultrasonic transducer transmits ultrasonic waves according to the applied drive signal, and receives ultrasonic echoes to output a reception signal.

Each ultrasonic transducer is configured by a vibrator in which electrodes are formed on both ends of a material having a piezoelectric property (piezoelectric material) such as a piezoelectric ceramic represented by PZT (Pb (lead) zirconate titanate), or a polymeric piezoelectric element represented by PVDF (polyvinylidene difluoride). When a pulsed or continuous wave voltage is applied to the electrodes of the vibrator, the piezoelectric material expands and contracts. By the expansion and contraction, pulsed or continuous wave ultrasonic waves are generated from the respective vibrators, and an ultrasonic beam is formed by synthesizing these ultrasonic waves. Further, the respective vibrators expand and contract by receiving propagating ultrasonic waves to generate electric signals. These electric signals are outputted as reception signals of the ultrasonic waves, and inputted via a cable to the ultrasonic imaging control division 40 (FIG. 1).

Referring to FIG. 1 again, a radiation imaging system will be explained.

The radiation imaging control division 30 includes a tube voltage/current control unit 31, a high-voltage generating unit 32, an A/D converter 33, and a radiation image data generating unit 34.

In the X-ray tube 10, the X-ray transparency is determined according to the tube voltage applied between the cathode and the anode, and the amount of X-ray emission is determined according to the time integration of the tube current flowing between the cathode and the anode. The tube voltage/current control unit 31 adjusts imaging conditions of the tube voltage, tube current, and so on according to target values. The target values of the tube voltage and the tube current may be manually adjusted by the operator by using the console 70. The high-voltage generating unit 32 generates a high voltage to be applied to the X-ray tube 10 under the control of the tube voltage/current control unit 31. The A/D converter 33 converts analog radiation detection signals output from the X-ray detecting unit 12 into digital radiation detection signals, and the radiation image data generating unit 34 generates radiation image data based on the radiation detection signals.

Next, an ultrasonic imaging system will be explained.

The ultrasonic imaging control division 40 includes a scan control unit 41, a transmission circuit 42, a reception circuit 43, an A/D converter 44, a signal processing unit 45, and a B-mode image data generating unit 46. Here, the transmission circuit 42 to B-mode image data generating unit 46 form ultrasonic imaging means.

The scan control unit 41 sets a frequency and voltages of the drive signals to be applied from the transmission circuit 42 to the respective ultrasonic transducers of the ultrasonic probe 16 to adjust a frequency and sound pressure of the ultrasonic waves to be transmitted, under the control of the movement control unit 20. Further, the scan control unit 41 has a transmission control function of sequentially setting transmission directions of ultrasonic beams and selecting transmission delay patterns according to the set transmission directions, and a reception control function of sequentially setting reception directions of ultrasonic echoes and selecting reception delay patterns according to the set reception directions.

Here, the transmission delay pattern refers to a delay time pattern to be provided to the drive signals so as to form an ultrasonic beam in a desired direction with the ultrasonic waves transmitted from the plural ultrasonic transducers of the ultrasonic probe 16, and the reception delay pattern refers to a delay time pattern to be provided to the reception signals for extracting ultrasonic echoes from the desired direction with the ultrasonic waves received by the plural ultrasonic transducers. Plural transmission delay patterns and plural reception delay patterns are stored in a memory or the like.

The transmission circuit 42 generates drive signals to be respectively applied to the plural ultrasonic transducers. In this regard, the transmission circuit 42 may adjust the amounts of delay of the drive signals and supply the drive signals to the ultrasonic probe 16 such that the ultrasonic waves transmitted from the plural ultrasonic transducers form an ultrasonic beam, or may supply drive signals to the ultrasonic probe 16 such that the ultrasonic waves transmitted at once from the plural ultrasonic transducers reach the entire imaging region of the object.

The reception circuit 43 amplifies the reception signals respectively output from the plural ultrasonic transducers, and the A/D converter 44 converts the analog reception signals amplified by the reception circuit 43 into digital reception signals. The signal processing unit 45 performs reception focus processing by providing the respective delay times to the reception signals based on the reception delay pattern selected by the scan control unit 41, and adding those reception signals to one another. Through the reception focus processing, sound ray signals, in which the focal point of the ultrasonic echoes is narrowed, are formed. Furthermore, the signal processing unit 45 performs envelope detection processing on the sound ray signals by using a detection circuit, a low-pass filter, and so on to generate envelope signals.

The B-mode image data generating unit 46 corrects attenuation of the envelope signals by distance according to the depths of the reflection positions of ultrasonic waves by using STC (sensitivity time gain control), and then, performs processing such as logarithmic compression and gain adjustment on the envelope signals to generate image data. Further, the B-mode image data generating unit 46 converts (raster-converts) the image data into image data that follows the normal scan system of television signals to generate B-mode image data.

The image processing unit 60 performs necessary image processing such as gradation process on the radiation image data outputted from the radiation imaging control division 30 and the B-mode image data outputted from the ultrasonic imaging control division 40 to generate image data for display. Thereby, a radiation image, and an ultrasonic image are displayed on the display units 61 and 62, respectively.

The console 70 is used by the operator to operate the medical imaging apparatus. The control unit 80 controls the respective parts based on the operation of the operator. So far, the movement control unit 20, the tube voltage/current control unit 31, the radiation image data generating unit 34, the scan control unit 41, the signal processing unit 45, the B-mode image data generating unit 46, the probe location/posture detecting unit 50, the image processing unit 60, and the control unit 80 are configured by a central processing unit (CPU) and software for actuating the CPU to execute various kinds of processing. However, they may be configured by digital circuits or analog circuits. The software (program) is stored in the storage unit 90 including a hard disk, memory, or the like. Further, the transmission delay patterns and the reception delay patterns to be selected by the scan control unit 41 may be stored in the storage unit 90.

Figure 3:
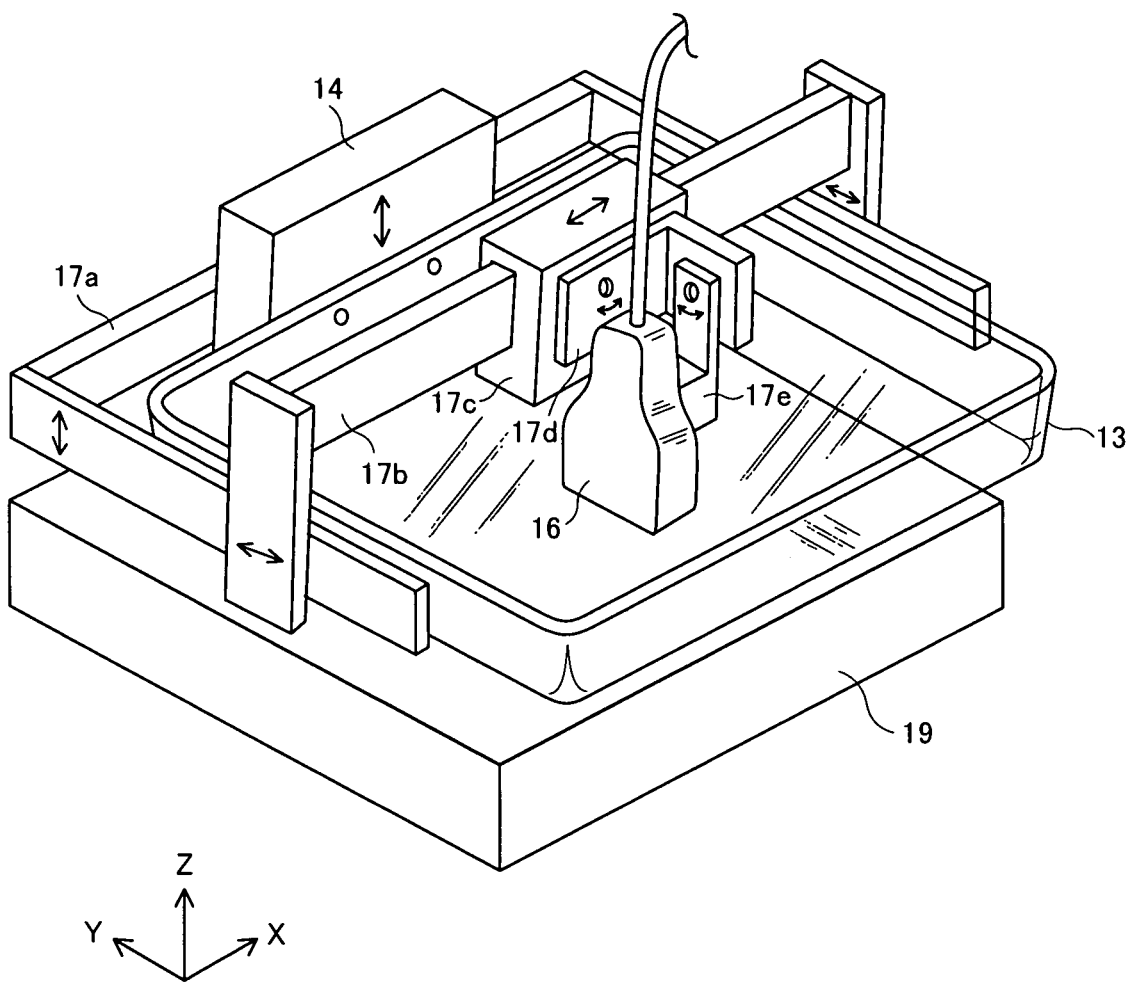
FIG. 3 is a perspective view for explanation of a probe movement mechanism of the medical imaging apparatus as shown in FIG. 1.

FIG. 3 is a perspective view for explanation of a probe movement mechanism of the medical imaging apparatus as shown in FIG. 1. Above the imaging stage 19, the compression plate 13 for compressing the object 1 between the imaging stage 19 and itself is supported by the compression plate movement mechanism 14. The compression plate movement mechanism 14 moves the compression plate 13 in the Z-axis direction under the control of the movement control unit 20. Furthermore, above the compression plate 13, the ultrasonic probe 16 moving along the upper surface of the compression plate 13 is supported by the probe movement mechanism.

The probe movement mechanism includes a first moving member 17a movable in the Z-axis direction, a second moving member 17b movable in the Y-axis direction relative to the first moving member 17a, a third moving member 17c movable in the X-axis direction relative to the second moving member 17b, a first rotating member 17d rotatable around the Y-axis direction relative to the third moving member 17c, and a second rotating member 17e rotatable around the X-axis direction relative to the first rotating member 17d. These moving members and rotating members are driven by stepping motors or the like under the control of the movement control unit 20.

Referring to FIG. 1 again, the compression plate movement mechanism 14 is provided with a compression plate location detecting unit 141 for detecting the location of the compression plate 13 in the Z-axis direction, and the probe movement mechanism 17 is provided with a probe location detecting unit 171 for detecting the location of the ultrasonic probe 16 in the Z-axis direction. Further, the locations of the ultrasonic probe 16 in the X-axis direction and the Y-axis direction are detected by the location sensor 18.

In the storage unit 90, an absolute coordinate of a home position of the compression plate 13 in the Z-axis direction and an absolute coordinate of a home position of the ultrasonic probe 16 in the Z-axis direction are registered in advance. The compression plate location detecting unit 141 detects a distance of the compression plate 13 from the home position in the Z-axis direction, and the probe location detecting unit 171 detects a distance of the ultrasonic probe 16 from the home position in the Z-axis direction. The movement control unit 20 calculates the distance between the compression plate 13 and the ultrasonic probe 16 based on detection results of the compression plate location detecting unit 141 and the probe location detecting unit 171, and controls the probe movement mechanism 17 such that the calculated distance takes a predetermined value.

Further, the location in the Z-axis direction and/or posture of the ultrasonic probe 16 relative to the compression plate 13 are detected with no contact by the probe location/posture detecting unit 50. For example, the probe location/posture detecting unit 50 detects the location and/or the posture of the ultrasonic probe 16 relative to the compression plate 13 based on the reflected image of the compression plate 13 in an ultrasonic image represented by the envelope signals generated by the signal processing unit 45 or the B-mode image data generated by the B-mode image data generating unit 46. Alternatively, the location and/or the posture of the ultrasonic probe 16 relative to the compression plate 13 may be optically detected by using a video camera as the probe location/posture detecting unit 50.

The movement control unit 20 controls the probe movement mechanism 17 based on a detection result of the probe location/posture detecting unit 50. Thereby, the location and/or the posture of the ultrasonic probe 16 relative to the compression plate 13 are controlled. When an air layer exists between the ultrasonic probe 16 and the compression plate 13, ultrasonic waves are reflected at a boundary of the air layer and no ultrasonic image can be generated. Accordingly, echo gel or the like is applied to the upper surface of the compression plate 13.

When ultrasonic imaging is performed, the probe movement mechanism 17 first sets the ultrasonic probe 16 in the home position and then moves the ultrasonic probe 16 in a predetermined direction. The ultrasonic probe 16 transmits and receives ultrasonic waves while moving, and thereby, ultrasonic imaging is performed. The compression plate 13 is bent and curved by compressing the object, and it is important to finely control the location and/or the posture of the ultrasonic probe 16 relative to the compression plate 13.

Figure 4A:
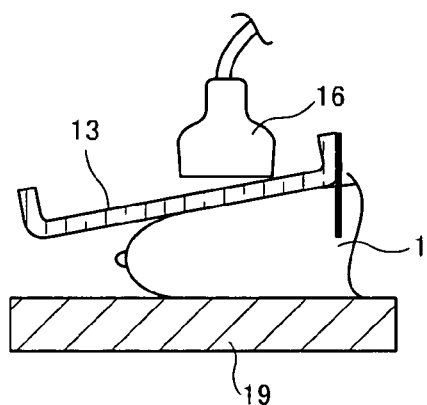
FIGS. 4A and 4B show a condition in which the ultrasonic probe is tilted relative to the compression plate within an ultrasonic slice plane and an ultrasonic image obtained in the condition, respectively.
Figure 4B:
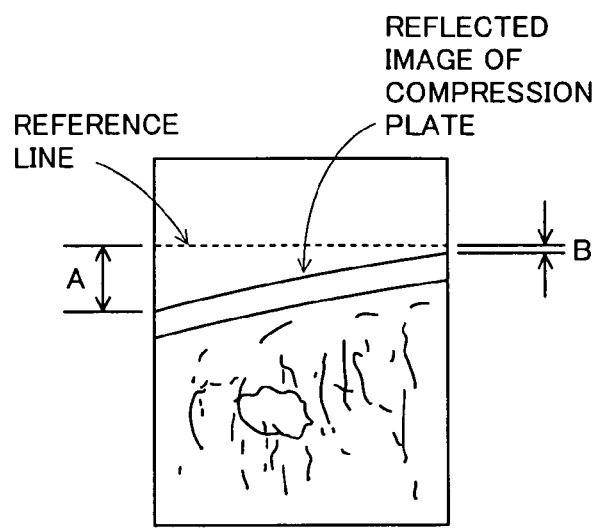

FIGS. 4A and 4B show a condition in which the ultrasonic probe is tilted relative to the compression plate within an ultrasonic slice plane and an ultrasonic image obtained in the condition. Here, the ultrasonic slice plane refers to a plane that passes the main arrangement direction (azimuth direction) of the plural ultrasonic transducers included in the ultrasonic probe 16 and is orthogonal to the ultrasonic transmission surface of the ultrasonic transducers. When the ultrasonic probe 16 is tilted relative to the compression plate 13 within the ultrasonic slice plane as shown in FIG. 4A, the reference line indicating the leading end of the ultrasonic probe 16 and the reflected image of the compression plate 13 are not in parallel to each other in the ultrasonic image shown in FIG. 4B.

Accordingly, the probe location/posture detecting unit 50 as shown in FIG. 1 obtains a measurement value "A" and a measurement value "B" by measuring distances between the reference line indicating the leading end of the ultrasonic probe 16 and the reflected image of the compression plate 13 in the ultrasonic image at plural locations (at the left end and the right end of the ultrasonic image in FIG. 4B), and detects a tilt of the ultrasonic probe 16 relative to the compression plate 13 within the ultrasonic slice plane based on a difference between the measurement value "A" and the measurement value "B". In place of the reference line indicating the leading end of the ultrasonic probe 16, another reference line in parallel to the reference line may be used.

Figure 5A:
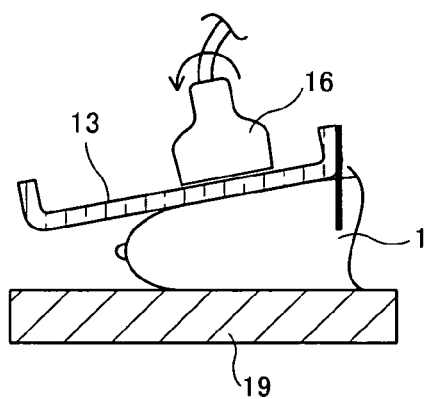
FIGS. 5A and 5B show a condition in which the ultrasonic probe is not tilted relative to the compression plate within the ultrasonic slice plane and an ultrasonic image obtained in the condition, respectively.
Figure 5B:
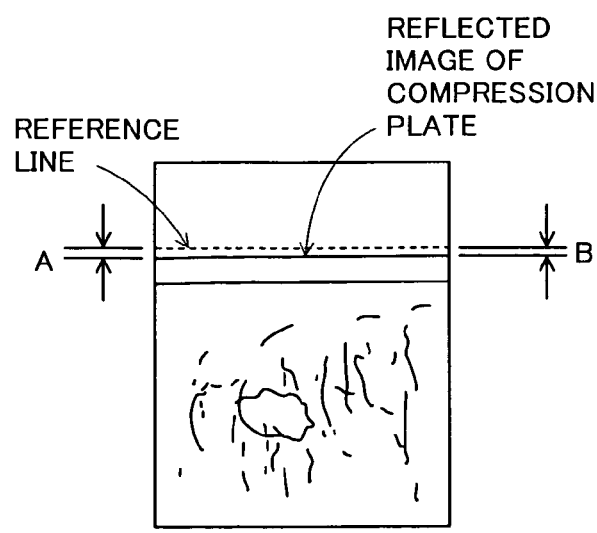

The movement control unit 20 as shown in FIG. 1 controls the probe movement mechanism 17 such that the measurement value "A" and the measurement value "B" satisfies A≈B based on the detection result of the probe location/posture detecting unit 50. Specifically, in FIG. 3, the angle of the second rotating member 17e around the X-axis is controlled. Thereby, the tilt of the ultrasonic probe 16 relative to the compression plate 13 within the ultrasonic slice plane is controlled to be minimum. As a result, the tilt of the ultrasonic probe 16 relative to the compression plate 13 is corrected as shown in FIG. 5A, and the reference line indicating the leading end of the ultrasonic probe 16 and the reflected image of the compression plate 13 are substantially in parallel to each other in the ultrasonic image as shown in FIG. 5B.

Figure 6A:
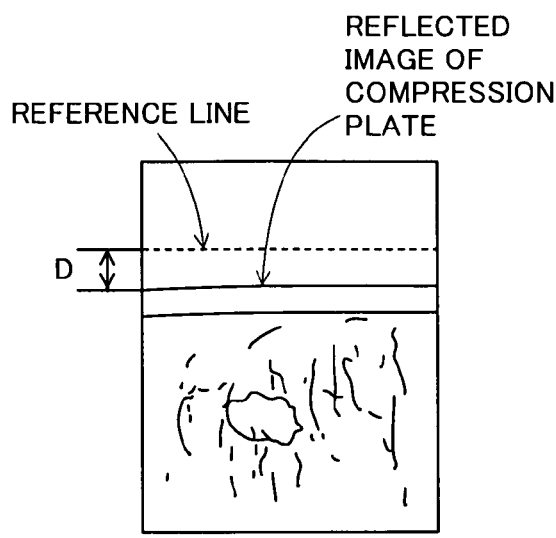
FIGS. 6A and 6B show ultrasonic images obtained in two conditions of different distances between the ultrasonic probe and the compression plate.
Figure 6B:
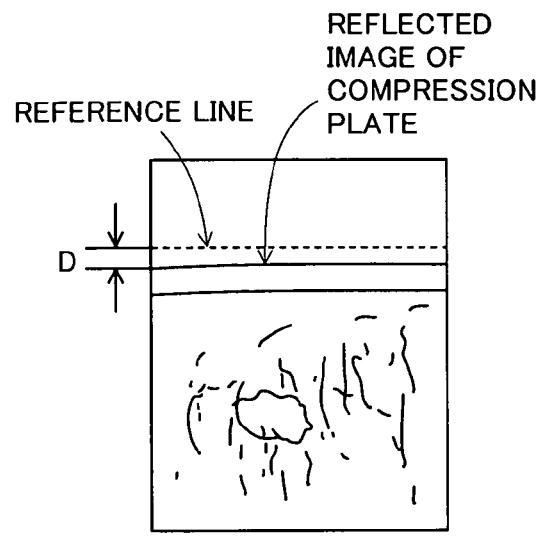

FIGS. 6A and 6B show ultrasonic images obtained in two conditions of different distances between the ultrasonic probe and the compression plate. The probe location/posture detecting unit 50 as shown in FIG. 1 obtains a measurement value "D" by measuring a distance between the reference line indicating the leading end of the ultrasonic probe 16 and the reflected image of the compression plate 13 in the ultrasonic image. When the ultrasonic probe 16 is a part from the compression plate 13, the measurement value "D" is a large value as shown in FIG. 6A.

The movement control unit 20 compares the measurement value "D" obtained by the probe location/posture detecting unit 50 with a predetermined value "C", and controls the probe movement mechanism 17 such that the measurement value "D" satisfies D≈C based on a comparison result thereof. Specifically, in FIG. 3, the location of the first moving member 17a in the Z-axis direction is controlled. Thereby, the distance between the ultrasonic probe 16 and the compression plate 13 is controlled to take the predetermined value "C". As a result, even when the compression plate 13 is curved in the traveling direction (X-axis direction) of the ultrasonic probe 16, the distance between the ultrasonic probe 16 and the compression plate 13 can be kept constant, and they can be prevented from contacting each other too strongly or separating from each other too distantly to cause acoustic disconnection.

Here, it is desirable that the predetermined value "C" is set equal to or more than zero and equal to or less than 2 mm to 3 mm. When the ultrasonic probe 16 is tilted relative to the compression plate 13 and plural different measurement values are obtained as shown in FIG. 4B, it is desirable that the minimum value of those measurement values is used as the measurement value "D". Further, when the compression plate 13 is curved and plural different measurement values are obtained, it is also desirable that the minimum value of those measurement values is used as the measurement value "D".

Figure 7A:
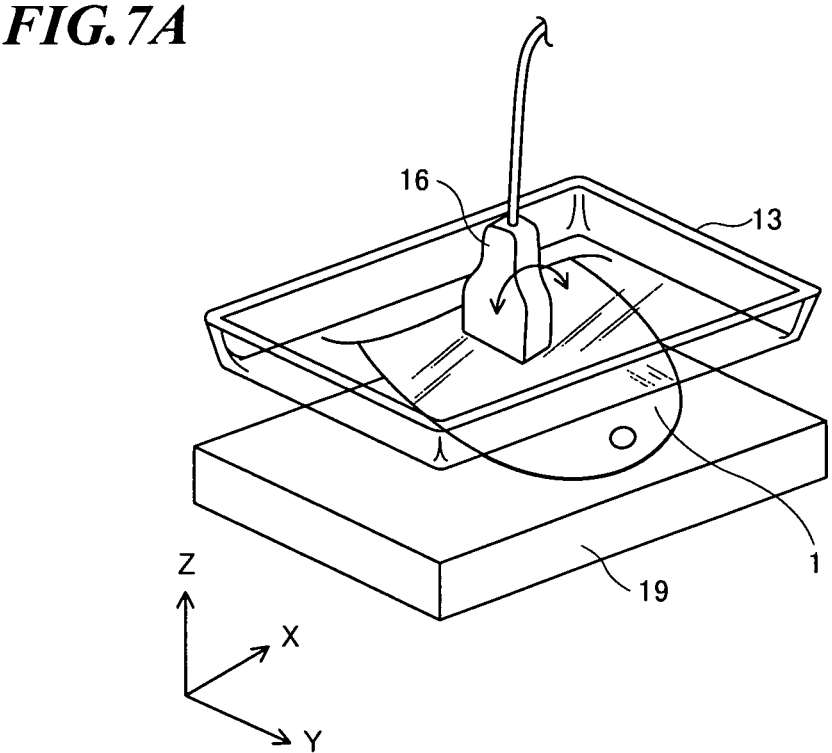
FIGS. 7A and 7B are diagrams for explanation of a method of controlling the tilt of the ultrasonic probe within a plane orthogonal to the ultrasonic slice plane.
Figure 7B:
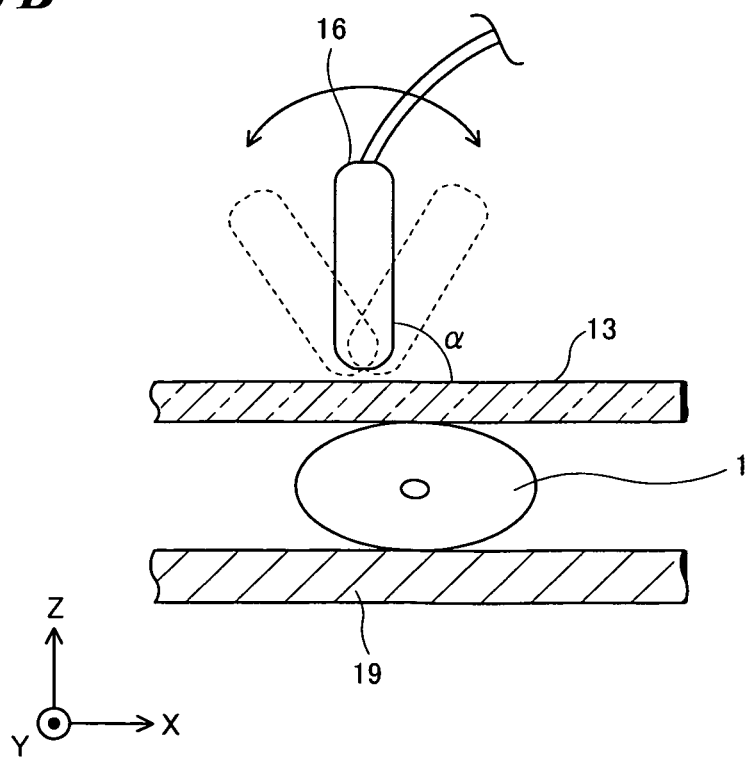

FIGS. 7A and 7B are diagrams for explanation of a method of controlling the tilt of the ultrasonic probe within a plane orthogonal to the ultrasonic slice plane, and FIG. 7A is a perspective view and FIG. 7B is a front sectional view. As shown in FIG. 7B, given that the angle formed by the ultrasonic probe 16 and the compression plate 13 within the plane (XZ plane) orthogonal to the ultrasonic slice plane is α, when α is apart from 90°, ultrasonic waves are diffused and image quality is deteriorated due to the influence of refraction and/or reflection of ultrasonic waves at the interface between the ultrasonic probe 16 and the compression plate 13 and/or the interface between the compression plate 13 and the object 1.

Accordingly, the probe location/posture detecting unit 50 shown in FIG. 1 detects intensity of the reception signal outputted from the ultrasonic probe 16 based on the reception signal outputted from the A/D converter 44, for example, and the movement control unit 20 controls the tilt of the ultrasonic probe 16 within the XZ plane such that the intensity of the reception signal detected by the probe location/posture detecting unit 50 becomes the maximum. Specifically, in FIG. 3, the angle of the first rotating member 17d around the Y-axis is controlled. Thereby, the angle α formed by the ultrasonic probe 16 and the compression plate 13 within the XZ plane is controlled to be substantially 90°.

In the above description, the case where the location and/or the posture of the ultrasonic probe 16 relative to the compression plate 13 is controlled in real time has been explained. However, the shape of the curved compression plate 13 may be measured in advance by pre-imaging the compression plate 13 in a state where the ultrasonic probe 16 is at a certain distance apart from the compression plate 13, and shape data may be stored in the storage unit 90 or the like, and then, the movement control unit 20 may move the ultrasonic probe 16 based on the shape data to perform ultrasonic imaging. Alternatively, by employing a one-and-a-half-dimensional transducer array or two-dimensional transducer array in the ultrasonic probe 16, during ultrasonic imaging of a certain region, pre-imaging of the adjacent regions may be performed.

According to the above-mentioned embodiment, even when the compression plate 13 is curved, the acoustic connection between the ultrasonic probe 16 and the compression plate 13 can be maintained, and partial image loss and image quality deterioration can be prevented. Further, the amount of echo gel or the like applied to the compression plate 13 may be smaller. Furthermore, the influence of the friction between the ultrasonic probe 16 and the compression plate 13 can be reduced, and scratches and abrasions on the respective parts due to friction can be prevented.

The invention claimed is:

1. A medical imaging apparatus comprising:
    an imaging stage configured to mount an object to be inspected;
    a compression plate having a first surface configured to compress the object and a second surface opposed to the first surface, and configured to compress the object between said imaging stage and itself;
    an ultrasonic probe provided to maintain acoustic connection to the second surface of said compression plate, and configured to transmit ultrasonic waves according to drive signals and receive ultrasonic echoes to output reception signals;
    an ultrasonic imaging unit configured to supply the drive signals to said ultrasonic probe and generate image data representing an ultrasonic image based on the reception signals outputted from said ultrasonic probe;
    a probe movement mechanism configured to translate and rotate said ultrasonic probe to adjust a location and/or a posture of said ultrasonic probe relative to said compression plate;
    a detecting unit configured to detect the location and/or the posture of said ultrasonic probe relative to said compression plate; and
    a control unit configured to control said probe movement mechanism based on a detection result of said detecting unit to keep a leading end of said ultrasonic probe substantially in parallel with the second surface of said compression plate at a constant distance therebetween without said ultrasonic probe and said probe movement mechanism contacting said compression plate.

2. The medical imaging apparatus according to claim 1, wherein said detecting unit is configured to identify a reflected image of the second surface of said compression plate in the ultrasonic image based on brightness of the ultrasonic image, and detect the location and/or the posture of said ultrasonic probe relative to said compression plate based on the reflected image of the second surface of said compression plate in the ultrasonic image.

3. The medical imaging apparatus according to claim 1, wherein:
    said detecting unit is configured to obtain measurement values by identifying a reference line indicating the leading end of said ultrasonic probe in the ultrasonic image, identifying a reflected image of the second surface of said compression plate in the ultrasonic image based on brightness of the ultrasonic image, and measuring distances between the reference line and the reflected image of the second surface of said compression plate at plural positions, and configured to detect a tilt of said ultrasonic probe relative to said compression plate within an ultrasonic slice plane based on a difference between the measurement values at the plural positions, and
    said control unit is configured to control said probe movement mechanism to adjust the tilt of said ultrasonic probe relative to said compression plate within the ultrasonic slice plane based on the detection result of said detecting unit.

4. The medical imaging apparatus according to claim 1, wherein:
   said detecting unit is configured to obtain a measurement value by identifying a reference line indicating the leading end of said ultrasonic probe in the ultrasonic image, identifying a reflected image of the second surface of said compression plate in the ultrasonic image based on brightness of the ultrasonic image, and measuring a distance between the reference line and the reflected image of the second surface of said compression plate, and
   said control unit is configured to compare the measurement value obtained by said detecting unit to a predetermined value and control said probe movement mechanism to adjust the distance between said ultrasonic probe and the second surface of said compression plate based on a comparison result.

5. The medical imaging apparatus according to claim 1, wherein:
   said detecting unit is configured to detect intensity of the reception signals outputted from said ultrasonic probe, and
   said control unit is configured to control said probe movement mechanism to adjust a tilt of said ultrasonic probe such that the intensity of the reception signals detected by said detecting unit becomes maximum.

* * * * *